(12) United States Patent
Annis et al.

(10) Patent No.: US 8,192,396 B2
(45) Date of Patent: *Jun. 5, 2012

(54) CONNECTOR DEVICE

(75) Inventors: Larry D. Annis, Elgin, IL (US); Richard Rollin, Menzingen (CH)

(73) Assignee: Medela Holding AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/902,004

(22) Filed: Oct. 11, 2010

(65) Prior Publication Data

US 2011/0028893 A1 Feb. 3, 2011

Related U.S. Application Data

(63) Continuation of application No. 12/011,269, filed on Jan. 25, 2008, now Pat. No. 7,824,362, and a continuation of application No. 10/600,078, filed on Jun. 20, 2003, now Pat. No. 7,357,782.

(60) Provisional application No. 60/397,439, filed on Jul. 19, 2002.

(51) Int. Cl.
*A61M 1/06* (2006.01)

(52) U.S. Cl. ............. 604/74; 604/346; 285/133.21

(58) Field of Classification Search .......... 604/74, 604/346; 285/45, 55, 133.11, 133.21, 133.3
See application file for complete search history.

(56) References Cited

U.S. PATENT DOCUMENTS

| 4,759,747 | A | * | 7/1988 | Aida et al. | 604/74 |
| 5,007,899 | A | * | 4/1991 | Larsson | 604/74 |
| 5,071,403 | A | * | 12/1991 | Larsson | 604/74 |
| 5,797,875 | A | * | 8/1998 | Silver | 604/74 |
| 7,357,782 | B2 | * | 4/2008 | Rollin et al. | 604/74 |
| 7,824,362 | B2 | * | 11/2010 | Annis et al. | 604/74 |

* cited by examiner

*Primary Examiner* — Lynne Anderson
(74) *Attorney, Agent, or Firm* — McDonnell Boehnen Hulbert & Berghoff LLP

(57) ABSTRACT

An adapter for use in connecting a vacuum source with a breast shield is disclosed including a housing with at least one female coupling component formed therein, at least one male coupling component that is adapted to attach to a tube at one end for conveying pressure from the vacuum source, while the other end is sized and shaped to be received in the female coupling component. A passageway extends between the first end and the second end of the male coupling component for conveying the pressure. The female coupling component is defined therein by an interior sidewall that has a channel formed therein open to the female coupling component at least somewhere along the interior sidewall. When the male coupling component is inserted in the female coupling component, a sealing portion of the male coupling component engages the interior sidewall surface such that ambient air is prevented from entering the channel and disrupting optimal vacuum pressure.

2 Claims, 8 Drawing Sheets

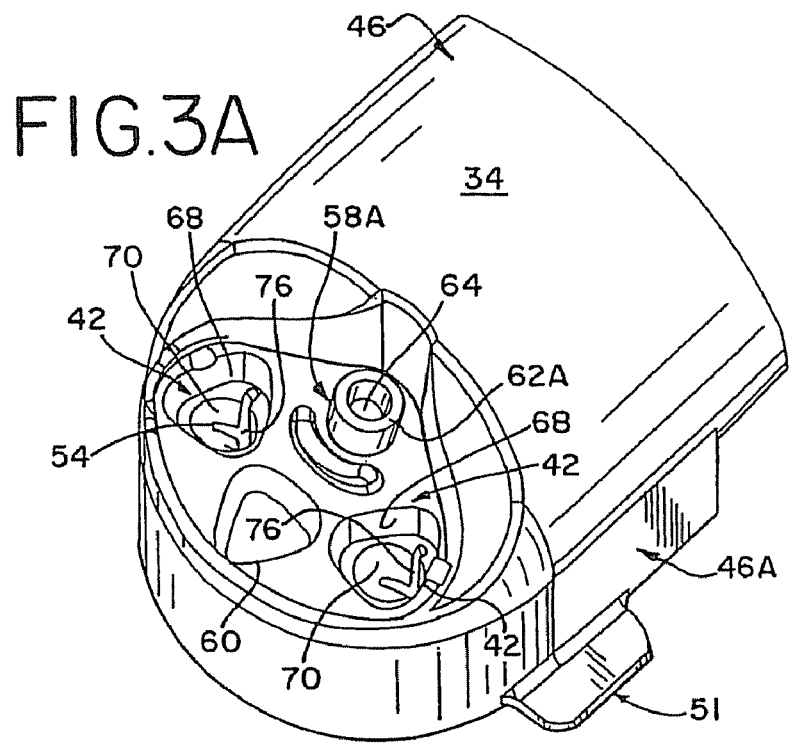
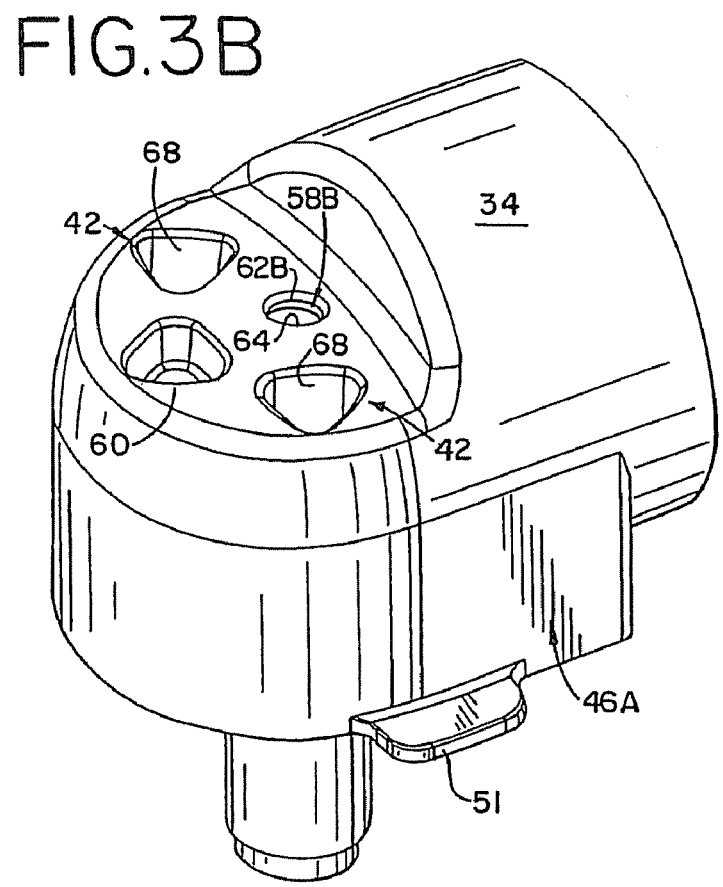

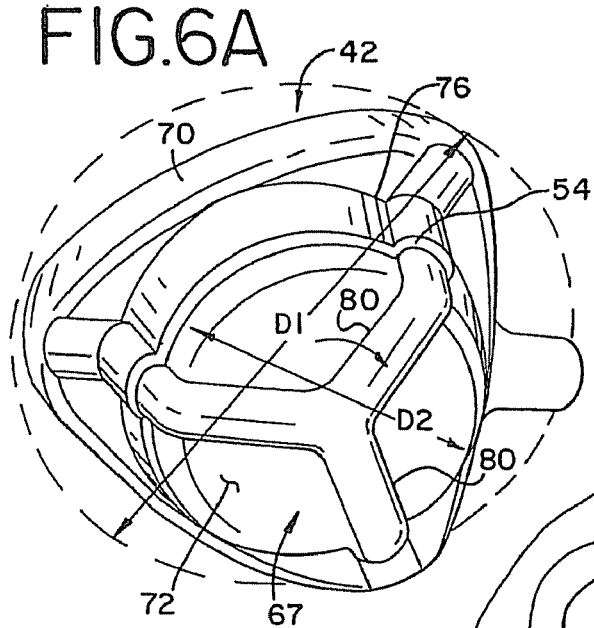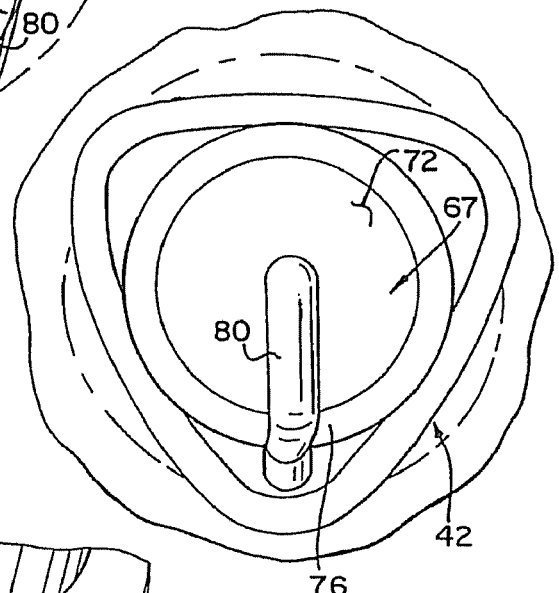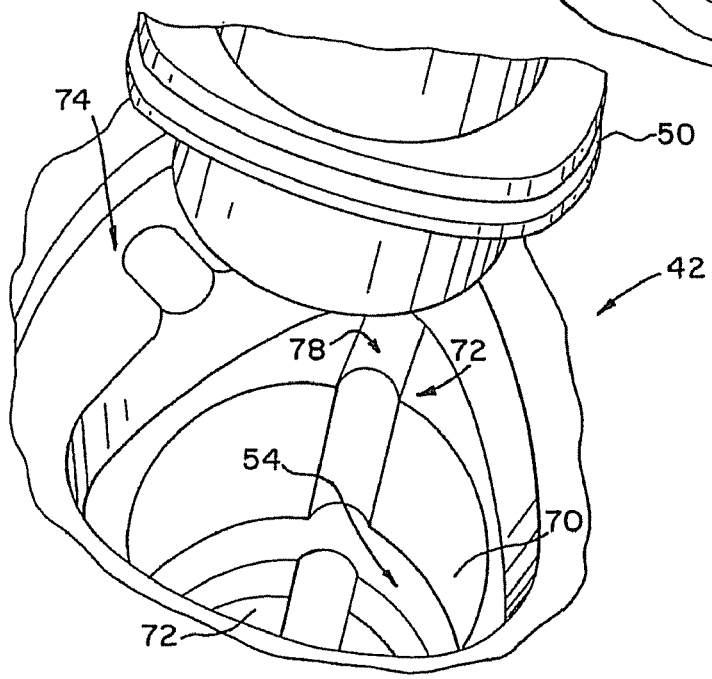

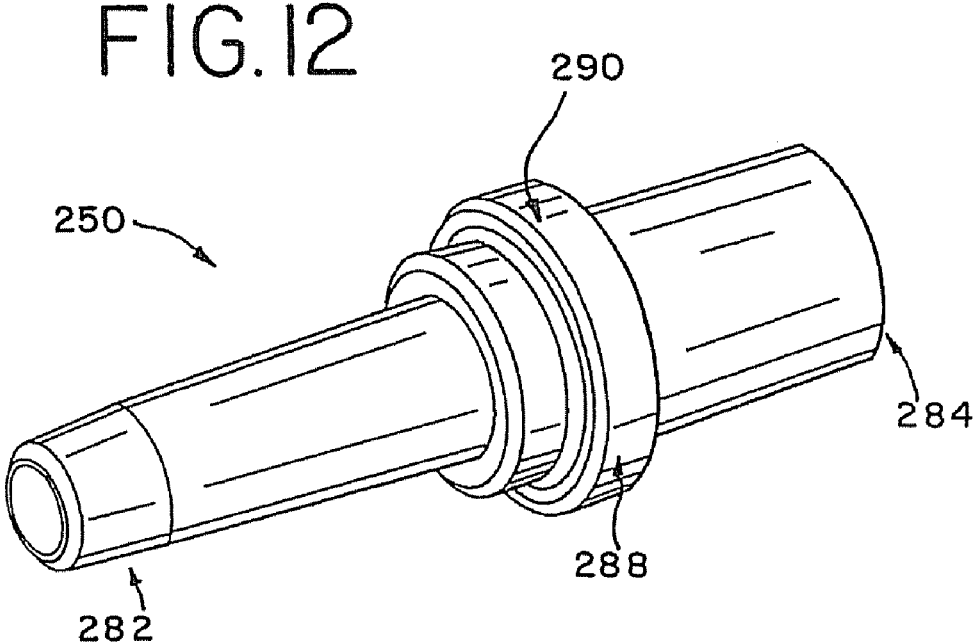
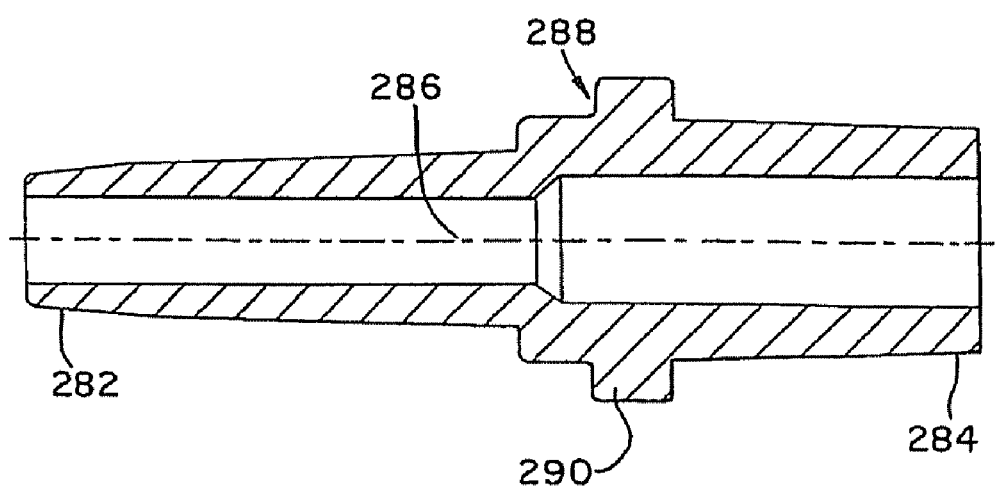

CONNECTOR DEVICE

This application claims benefit of U.S. Provisional Application No. 60/397,439 filed Jul. 19, 2002.

FIELD OF THE INVENTION

This invention is directed generally to breast pump assemblies and, more particularly, to an improved adapter for use within a breast pump assembly.

BACKGROUND OF THE INVENTION

Breast pump assemblies for extracting or expressing breast milk from a woman's breasts for later use to feed by an infant, have been available for years. Typically, these breast pump assemblies include a source of reduced pressure or vacuum, and at least one milking unit, which is includes a funnel-shaped hood, or breast shield, and a storage container. The breast shield is placed over the women's nipple and a substantial portion of the breast. A reduced pressure or vacuum is intermittently generated in the breast shield in a manner that causes milk to be expressed from the breast. The milk then typically flows to the storage container for later use. Although vacuum is what is typically employed in the operation of a breast pump assembly, positive pressure may also be conveyed in desired applications.

Generally, two types of breast pump assemblies have been marketed for use by nursing women: manually operated breast pump assemblies; and motor-driven breast pump assemblies. In manually operated breast pump assemblies, the intermittent vacuum is typically generated by means of a piston type pump. The piston pump generally includes a piston cylinder, which is connected to the breast shield, and a piston, slidably disposed within the piston cylinder. The piston has a hand-drivable piston rod connected thereto by which a person operating the breast pump assembly can manually move the piston back and forth within the piston cylinder, thus generating the vacuum. The intermittent vacuum in motor-driven breast pump assemblies is typically generated by a similar piston pump, but the piston pump is connected to an electrically powered motor drive unit, and the motor drive unit moves the piston back and forth within the piston cylinder. There is a breast pump assembly sold by Medela, Inc. under the mark LACTINA®, which has a motor drive unit adapted for operating a piston pump which could otherwise be used for a manually operated breast pump assembly. An example of this manual, yet also motorized breast pump assembly is disclosed in U.S. Pat. No. 5,007,899 ("the '899 patent"). The motor drive unit is separate from the breast shield. The vacuum generated when the motor drive unit moves the piston back and forth within the piston cylinder is transmitted to the breast shield through plastic tubing, which is connected to both the breast shield and the piston pump. The plastic tubing is often connected to the piston pump and/or the breast shield by use of an adapter. Because of the transfer of air throughout the breast pump assembly, the adapter must provide an airtight seal. Additionally, the user should be able to easily manipulate the adapter.

In the type of breast pump assembly disclosed in the '899 patent, where the breast shield can be used in a manual or a motorized mode, the breast shields and their pumps must be precisely matched in order to provide a safe and efficiently operating unit. The piston pumps used with the '899 patent breast pump assembly are, for example, precisely tuned to the operational function of the breast shield used therewith, as, for instance, concerning the volume of air moved in the cyclical action of the pump. Use of a different pump or breast shield can adversely affect the use of the subject breast pump assembly.

Accordingly, there is a demand for an adapter that provides a means for precisely matching breast shields and corresponding pumps. The present invention satisfies this demand.

SUMMARY OF THE INVENTION

It is an object of the present invention to provide an improved adapter for use in a breast pump assembly that not only provides an airtight seal, but also serves as a means to prevent connection of unmatched and potentially deleterious components.

Another object of the present invention is to provide an improved female coupling component for use in the above-mentioned adapter.

A further object of the present invention is to provide an improved male coupling component for use in the above-mentioned adapter.

An additional object of the present invention is to provide a novel method of engaging male and female coupling components of an adapter, which provides an airtight seal and prevents connection of unmatched and potentially deleterious components.

One embodiment of the present invention provides an adapter for use in connecting a motor driven piston pump—that is, a fluid pressure or vacuum source—with a breast pump assembly. The adapter comprises in part a cap portion, which sealingly engages a piston cylinder of the piston pump. The cap portion defines, in part, a vacuum chamber therein which communicates with the interior of the piston cylinder and a lower well of the female coupling component, described in more detail hereinafter.

The adapter further comprises a male coupling component including a longitudinal axis having a first end and a second end. The male coupling component can be removably or fixedly attached at its first end to a tube for conveying the fluid pressure from the fluid pressure source. A passageway extends between the first end and the second end for further conveying the fluid pressure. A radially outwardly extending sealing portion is formed on an exterior surface of the male coupling component spaced from the second end.

The adapter further comprises a female coupling component sized and shaped for receiving the male coupling component. The female coupling component includes upper surfaces and lower surfaces, and a rim surface. The upper surface and the lower surface are sized and shaped such that the female coupling component can receive the male coupling component therein.

The upper surface of the female coupling component defines an upper well having a first general diameter. The upper well is sized and shaped to match the size and shape of the radially outwardly extending sealing portion. When the male coupling component is received in the female coupling component, the sealing portion of the male coupling component is received in the upper well. Because the upper well matches the size and shape of the radially outwardly extending sealing portion, when the sealing portion of the male coupling component is received in the upper well, the upper surface engages a sealing surface of the sealing portion to form an airtight seal.

The lower surface of the female coupling component defines a lower well with a second general diameter, which is less than the first general diameter of the upper well. The lower well is sized and shaped to receive the second end of the male coupling component therein. The lower well is connected to the upper well by a rim surface. A channel is formed in the lower surface of the female coupling component. The channel includes an opening in the rim surface and is open at least at one point along the lower surface. The lower surface also includes a port therein which allows communication between the lower well and the vacuum chamber.

When the upper surface and the sealing surface of the sealing portion are sealingly engaged, ambient air is prevented from being drawn into the female coupling component, thereby permitting the pump to work at its optimal operating vacuum. When an unmatched male coupling component is used, ambient air is drawn into the upper well and is transmitted into the lower well through the channel, and then through the port, into the vacuum chamber, thus preventing the breast pump assembly from working at its optimal operating vacuum. Therefore, use of unmatched components can be potentially harmful.

These and other features and advantages of the present invention will be further understood upon consideration of the following detailed description of an embodiment of the present invention, taken in conjunction with the accompanying drawings, in which:

BRIEF DESCRIPTION OF THE DRAWINGS

FIG. 3A is an overhead view of the adapter of FIG. 2;

FIG. 3B is a perspective view of a second embodiment of an adapter;

FIG. 6A is an overhead perspective of one embodiment of a female coupling component, used in accordance with the present invention;

FIG. 6B is an overhead perspective of a second embodiment of a female coupling component, used in accordance with the present invention;

FIG. 7 is another overhead perspective of a female coupling component, used in accordance with the present invention, showing a connector entering the coupling component;

FIG. 12 is a perspective view of another male coupling component, as used in the present invention;

FIG. 13 is a cross-sectional view of the male coupling components of FIG. 12.

DETAILED DESCRIPTION OF INVENTION

Figure 1:
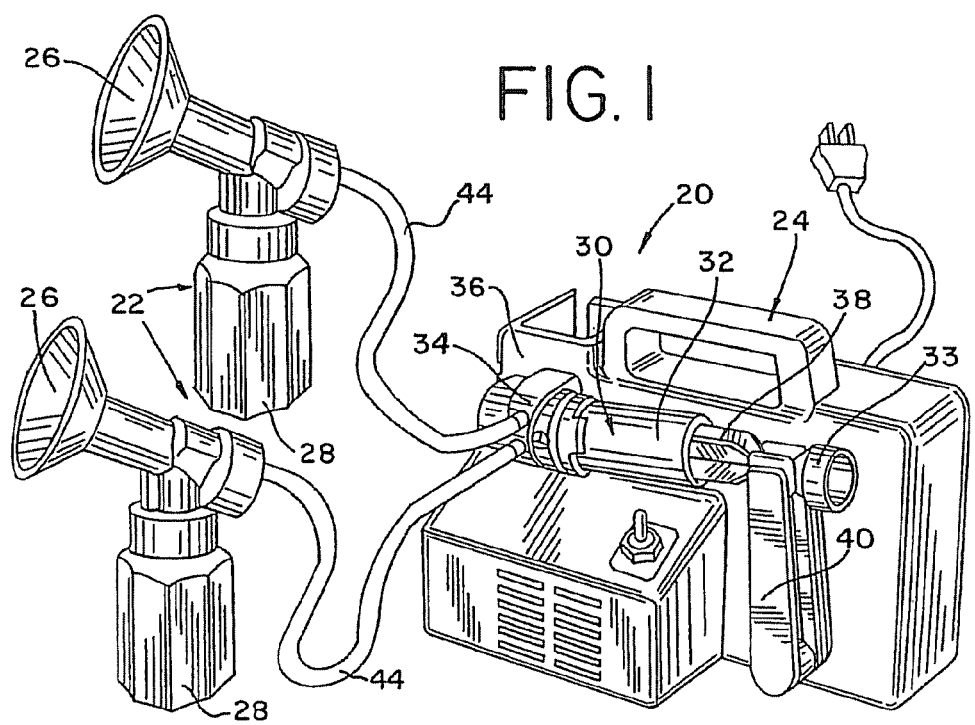
FIG. 1 is a perspective view showing a preferred embodiment of a breast pump assembly of the kind incorporating the present invention.

FIG. 1 illustrates, generally, the usage of one embodiment of the present invention within a breast pump assembly. One embodiment of a breast pump assembly 20 is shown in FIG. 1, and includes two milking units 22 and a motor drive unit 24. Each milking unit 22 includes a breast shield 26 and a container 28, such as a bottle, for collecting and storing the breast milk, which is connected to the lower portion of the breast shield 26. The milking units 22 are adapted to be used with a piston pump 30. A piston cylinder 32 of the piston pump 30 is connectable to the breast shield 26 to operate the milking unit 22 in a manually driven mode (i.e., the piston pump is reciprocated by hand). The piston cylinder 32 can be connected to the breast shield 26 directly, or by way of tubes 44 which can be attached to a tube attaching means (not shown) on the breast shield 26. Details of this type of breast pump assembly and the piston pump can be gleaned from U.S. Pat. Nos. 4,929,229 and 4,857,051.

The motor drive unit 24 is also adapted to receive and hold and to mechanically operate the piston pump 30. The motor drive unit 24 is substantially as shown and described in U.S. Pat. No. 5,007,899.

An improved cylinder holder, or adapter 34 of the present invention is attachable to the casing 36 of the motor drive unit 24. The piston cylinder 32 is received in the adapter 34. A piston 33, having a piston rod 38 extending therefrom, is slidably disposed within the piston cylinder 32 and the piston rod 38 is releasably held at one end of an arm 40. Arm 40 is mounted at its other end to the casing 36 of the motor drive unit 24 for reciprocal movement of the piston rod 38. As will be described in detail below, the adapter 34 includes female coupling components 42 (See FIGS. 3A and 3B) for removably connecting tubes 44 to the breast shields 26 of the respective milking units 22, via male coupling components 50 (See FIG. 2).

In brief, the motor drive unit 24 reciprocally moves the piston rod 38, thus moving the piston 33 back and forth within the piston cylinder 32. A rearward stroke of the piston rod 38 and thereby piston 33, that is, such that the piston 33 is moved to a position where it is partially exposed from the cylinder 32, generates a pressure change (usually a negative pressure) that is transmitted through the adapter 34 and the tubes 44 to one or both of the milking units 22.

Figure 4:
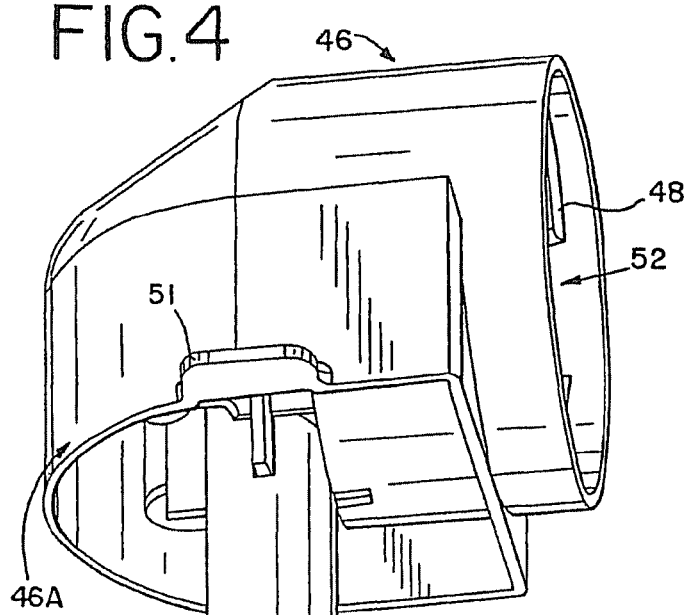
FIG. 4 is another perspective view of the adapter of FIG. 2.
Figure 5:
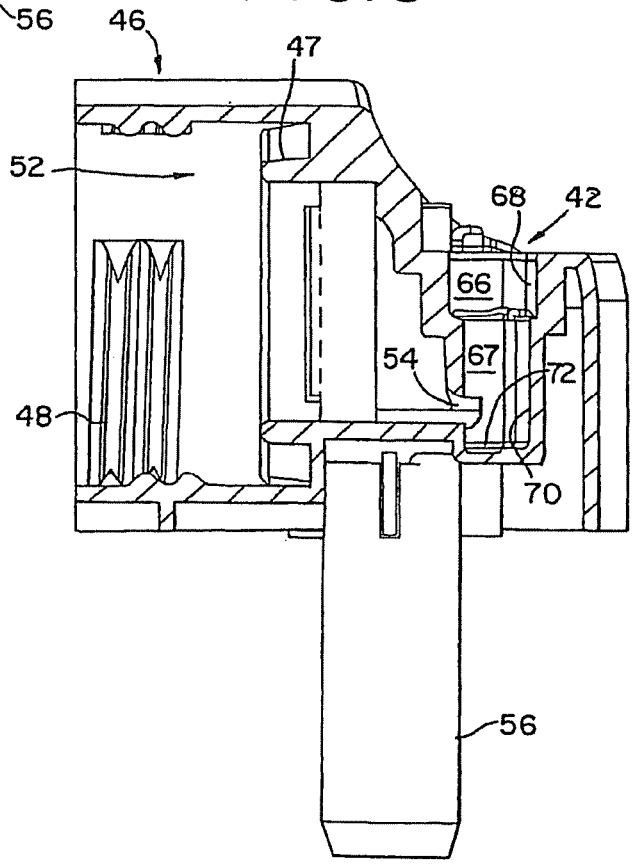
FIG. 5 a cross-sectional view of the adapter of FIG. 2.

As seen in FIGS. 2-5, the adapter 34 of the present invention includes a cap portion 46 that is match-threaded at 48 for substantially airtight attachment to the piston cylinder 32. FIG. 5 shows that the inside of the cap portion 46 of one embodiment of the invention includes a seal ring 47 disposed therein for sealing engagement with the piston cylinder 32. The cap portion 46, defines in part, a vacuum chamber 52 that communicates with the interior of the piston cylinder 32 and, through ports 54 with the interior of the female coupling components 42.

Further, the adapter 34 includes a post 56 that is removably received within a post hole (not shown) in the casing 36 to mount the adapter 34 to the motor drive unit 24. FIGS. 3A, 3B, and 4 show that the exterior sidewall 46A of the cap portion 46 includes a flange 51. The flange 51 slides into an enlarged slot (also not shown) when the post 56 is inserted in the post hole and the adapter 34 rotated into place (in a similar manner as described in the '899 patent). Other means for mounting the adapter to the casing can be readily employed, of course.

Figure 2:
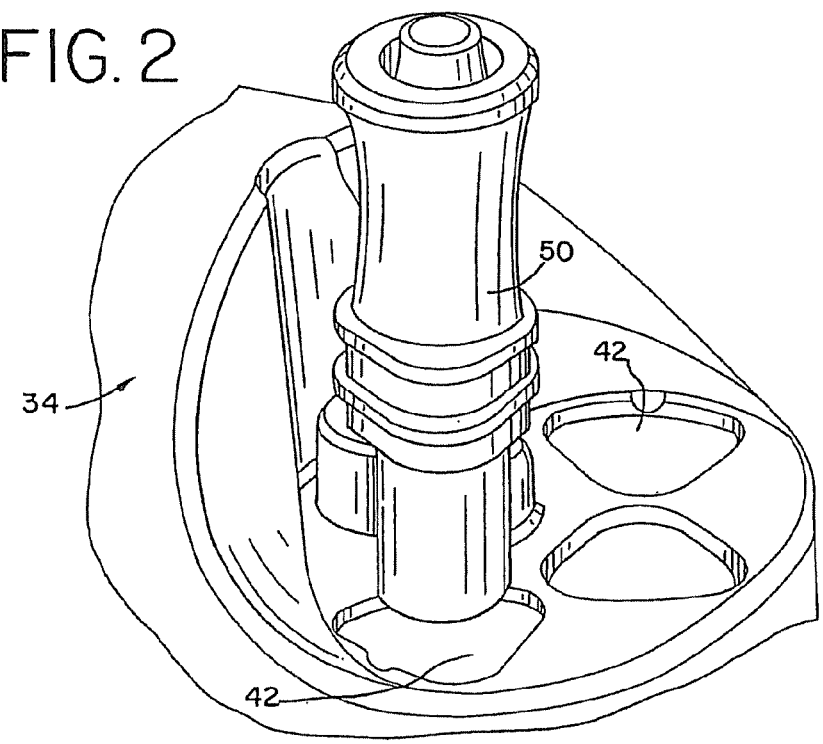
FIG. 2 is a perspective view of an adapter, in accordance with the present invention.

As shown in FIGS. 2, 3A, and 3B, adapter 34 generally includes female coupling components 42. The female coupling components 42 are sized and shaped to snugly receive mating male coupling components 50 (discussed in further detail below and shown in FIGS. 8-13), which are removably or fixedly attached to the ends of the tubes 44. This arrangement serves to provide an easily manipulated secure connection of the tubes 44 to the ports 54 in the female coupling components 42. For brevity, discussion will center on a single female coupling component 42, but it is understood that the coupling components 42 contain identical elements.

Referring to FIGS. 3A, 3B, and 5-8, the female coupling component 42 includes an upper surface 68, a lower surface 70, a bottom surface 72, and a rim surface 74. The upper surface 68 is sized and shaped to define an upper well 66 therein (FIG. 5). The lower surface 70 is sized and shaped to define a lower well 67 therein (FIG. 5). The lower surface 70 has a port 54 therein, through which air, or any fluid, can pass from the lower well 67 to the vacuum chamber 52, or vice versa. A channel 76 is formed in the lower surface 70 and is in communication with the port 54.

The upper well 66 has a diameter D1. The lower well 67 has a diameter D2. Diameter D1 is greater than diameter D2. The upper well 66 is connected to the lower well 67 by the rim surface 74. The channel 76 extends from an opening 78 in the rim surface 74 to the bottom surface 72 and is open to the lower well 67 at one or more points along the lower surface 70.

FIGS. 6A and 6B illustrate overhead detailed schematics of two embodiments of a female coupling component 42. The bottom surface 72 of the lower well 67 has at least one radially extending groove 80 formed therein. The groove 80 is in fluid communication with the channel 76 formed in the lower surface 70 and is open to the lower well 67 at one or more points along the bottom surface 72.

The upper well 66 is sized and shaped to receive and thereby provide a snug fit with the male coupling component 50. As depicted in one embodiment, the upper well 66 comprises a generally polygonal or slightly rounded triangular shape. It is understood however, that the upper well 66 can be of any shape provided it is sized to match a sealing portion 88 of a male coupling component 50 as will be described in further detail hereinafter.

Referring again to FIGS. 3A and 3B, adapter 34 also includes a stopper mount 58A, 58B and a stopper rest 60. Additionally, the stopper mount 58A further includes an aperture surface 62A, 62B that defines an aperture 64. As shown in FIG. 3A, the aperture surface 62A may extend outward from the adapter 34 such that stopper mount 58A is sized and shaped as an elevated cylinder. Alternatively, as shown in FIG. 3B, aperture surface 62B may extend inward into the adapter 34 such that stopper mount 58B is a well within the adapter 34. In accordance with one embodiment of the present invention, stopper mount 58A, 58B receives a mounting end 98A, 98B of stopper 96A, 96B (see FIGS. 14A, 14B, 14C and 14D) thereon, to mount the stopper 96A, 96B on the adapter 34.

Figure 14A:
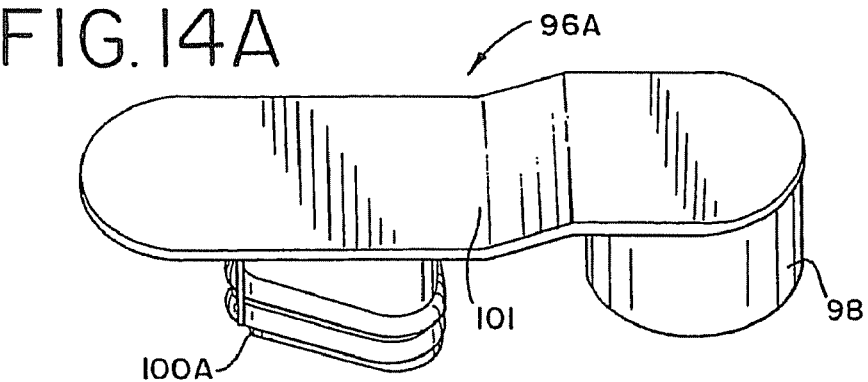
FIG. 14A is a perspective view of a stopper as used in accordance with the present invention.
Figure 14B:
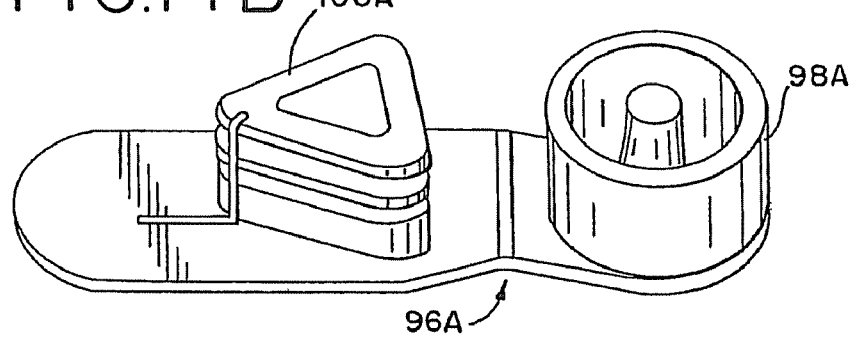
FIG. 14B is a perspective view of a stopper as used in accordance with the present invention.
Figures 14C, 14D:
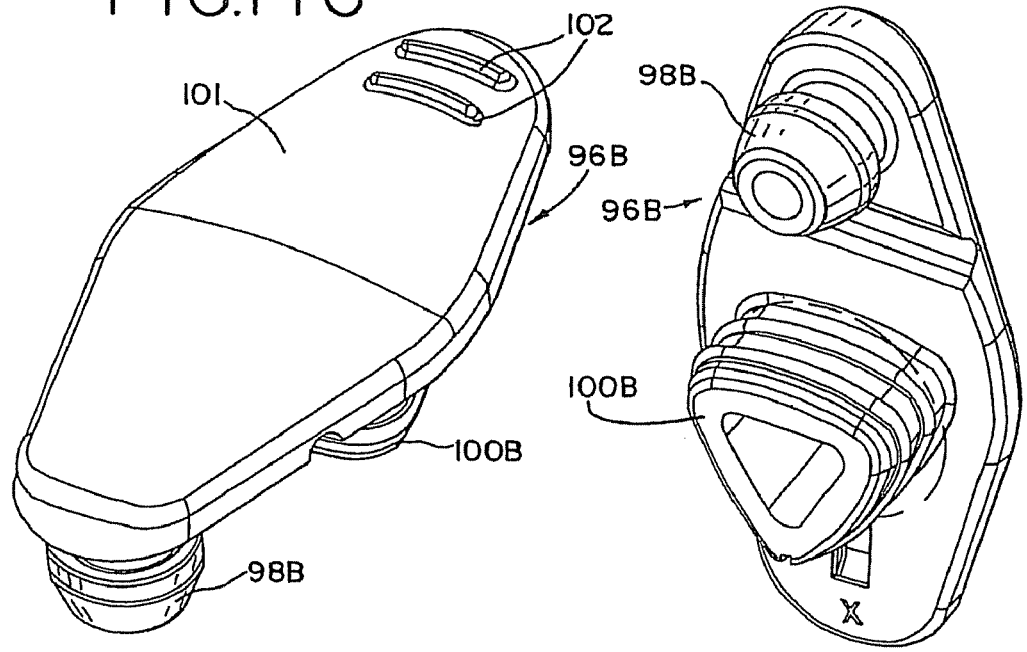
FIG. 14C is a perspective view of a stopper as used in accordance with the present invention.
FIG. 14D is a perspective view of a stopper as used in accordance with the present invention.

The stopper 96A, 96B is shown generally in FIGS. 14A, 14B, 14C and 14D. Plug 100A, 100B of stopper 96A, 96B may be placed, when not in use as a stopper, in the stopper rest 60. Preferably, stopper 96A, 96B is used to "cut off" one of multiple female coupling components 42 in the event that the user wishes to only utilize one of the milking units 22. Additionally, stopper 96A, 96B may include gripping ridges 102 on a top surface 101 as depicted in FIG. 14C.

As shown in FIG. 2, stopper rest 60 is similar in shape and size, to the upper well 66. The purpose for this is that the plug 100A, 100B of the stopper 96A, 96B is shaped similarly to a sealing portion 88 (see FIG. 8) to snugly fit into the stopper rest 60 (when not is use), and the upper well 66 of the female coupling component 42 (when in use).

As discussed earlier, tubes 44 are attached to male coupling components 50, which in turn may be inserted into corresponding female coupling components 42. This arrangement serves to provide an easily manipulatable and secure connection of tubes 44, via male coupling components 50, to adapter 34.

Figure 8:
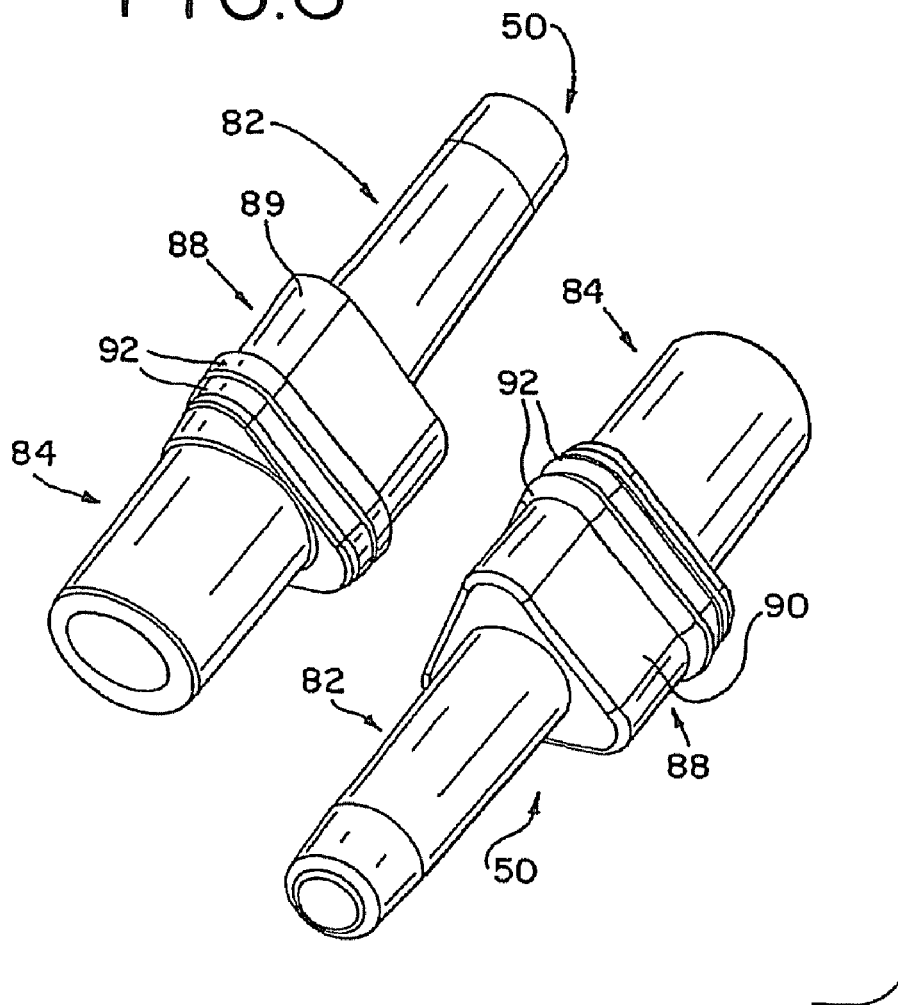
FIG. 8 is a perspective view of a pair of male coupling components, as used in the present invention.
Figure 9:
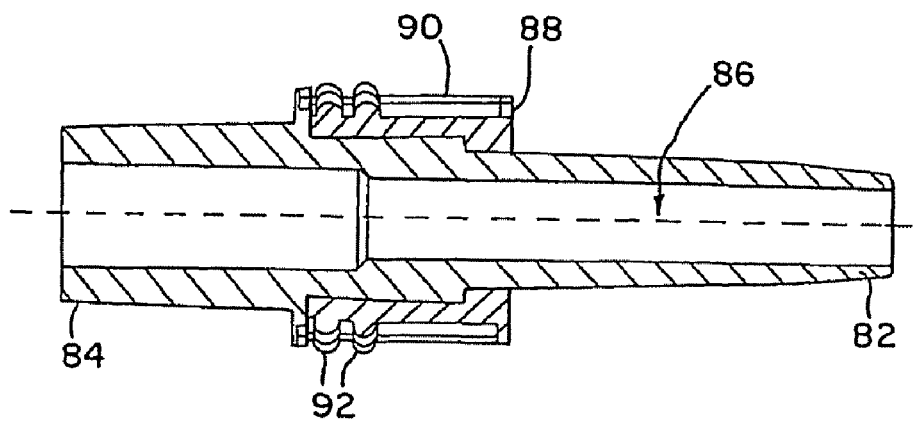
FIG. 9 is a cross-sectional view of the male coupling components of FIG. 8.

FIGS. 8-9 illustrate various perspectives of one embodiment of a male coupling component 50. As shown in detail in FIG. 8, male coupling component 50 is shown with a first end 82 to which a tube 44 is attached, and a second end 84. A passageway 86 extends through the male coupling component 50 between the first end 82 and the second end 84 for conveying the fluid pressure. Additionally, the connector 50 includes a radially outwardly extending sealing portion 88 formed on the male coupling component 50 between the first end 82 and the second end 84 and spaced from the second end 84. As shown in FIG. 8, the sealing portion 88 can be of a generally polygonal or slightly rounded triangular shape. It is understood, however, that the sealing portion 88 can be of any shape, so long as it matches the shape of the upper well 66 of the female coupling component 42. The sealing portion 88 also has a sealing surface 90 that includes at least one circumferential sealing ring 92 thereon, which engages the upper surface 68 of the upper well 66 to form a substantially airtight seal such that ambient air is prevented from entering the female coupling component 42. The upper surface 68 may include at least one circumferential groove (not shown) therein that engages with the circumferential sealing ring 92 to form the substantially airtight seal.

Figure 10:
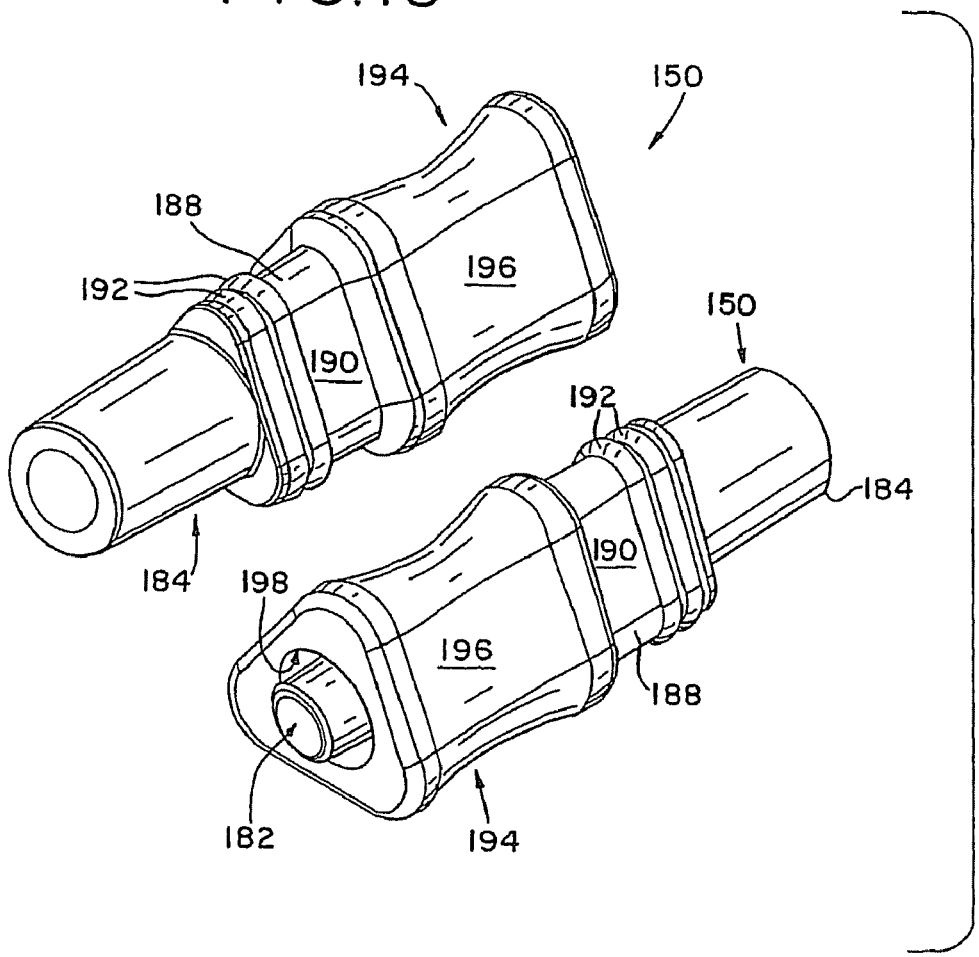
FIG. 10 is a perspective view of another pair of male coupling component, as used in the present invention.
Figure 11:
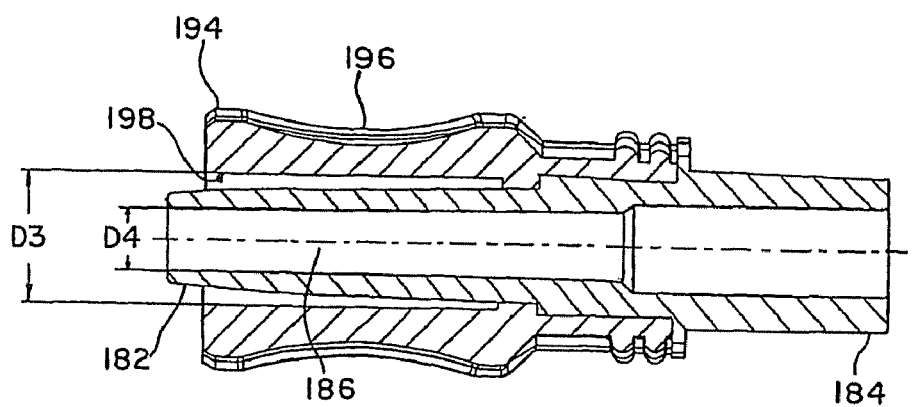
FIG. 11 is a cross-sectional view of the male coupling components of FIG. 10.

FIGS. 10-11 illustrate various perspectives of another embodiment of a male coupling component 150. As shown in detail in FIG. 10, male coupling component 150 is shown with a first end 182 to which a vacuum tube 44 is attached, and a second end 184. A gripping portion 194 surrounds the first end 182. FIGS. 10 & 11 show that the gripping portion 194 has a slightly concaved exterior surface 196 and a cylindrical interior surface 198 with a diameter D3 greater than diameter D4 of the first end 182 such that a tube 44 can be attached to the first end 182, yet snugly received within the interior surface 198 of the gripping portion 194. A passageway 186 extends through the male coupling component 150 between the first end 182 and the second end 184 for conveying the fluid pressure. Additionally, the male coupling component 150 includes a radially outwardly extending sealing portion 188 formed on the male coupling component 150 between the first end 182 and the second end 184, spaced from the second end 184. The sealing portion 188 can be of any shape so long as it is sized and shaped to match the size and shape of the upper well 66 of the female coupling component 42, but is depicted as having a generally polygonal or slightly rounded triangular shape. The sealing portion 188 has a sealing surface 190 that includes at least one circumferential sealing ring 192 thereon, which engages the upper surface 68 of the upper well 66 to form a substantially airtight seal such that ambient air is prevented from entering the female coupling component 42. The upper surface 68 may include at least one circumferential groove (not shown) therein that engages with the circumferential sealing ring 192 to form the substantially airtight seal.

FIGS. 12-13 illustrate various perspectives of yet another embodiment of a male coupling component 250. As shown in detail in FIG. 12, male coupling component 250 is shown with a first end 282 to which a tube 44 is attached, and a second end 284. A passageway 286 extends through the male coupling component 250 between the first end 282 and the second end 284 for conveying the fluid pressure. Additionally, the connector 250 includes a radially outwardly extending sealing portion 288 formed on the male coupling component 250 between the first end 282 and the second end 284, spaced from the second end 284. The sealing portion 288 can be of any shape, so long as it is sized and shaped to match the size and shape of the upper well 66 of the female coupling component 42, but is depicted as having a generally circular shape. The sealing portion 288 has a sealing surface 290 that engages the upper surface 68 of the upper well 66 to form a substantially airtight seal such that ambient air is prevented from entering the coupling component 42.

As a result of the unique design of the male coupling components 50 and the female coupling components 42, described above, the present invention provides for a unique fit between the male coupling components 50 and the female coupling components 42. This unique design assures that only this coupling component and connector will be successfully mated, thereby assuring that only properly matched equipment will be used.

It should be appreciated that the embodiments described above are to be considered in all respects only illustrative and not restrictive. The scope of the invention is indicated by the following claims rather than by the foregoing description. All changes that come within the meaning and range of equivalents are to be embraced within their scope.

We claim:

1. A male coupling component for use in connecting a breast shield with tubing to a vacuum source comprising:
   a first end, wherein said first end is sized and shaped to be attachable to said tubing;
   a second end, wherein said second end has an end diameter and is sized and shaped to be received in a female coupling component, wherein said female coupling component is defined by an interior sidewall surface that is in communication with the vacuum source, wherein said interior sidewall surface has an upper well with a first sidewall diameter, and a lower well with a second sidewall diameter, said second sidewall diameter being less than said first sidewall diameter, and a rim portion between said upper well and said lower well connecting said upper well and said lower well, said lower well including one or more ports formed therein allowing communication of said lower well with the vacuum source, and one or more channels formed therein communicating between said one or more ports and an opening in said rim portion;
   a passageway extending between said first end and said second end; and
   a sealing portion between said first end and said second end, said sealing portion having a sealing surface formed about a periphery thereof, said sealing portion having a sealing diameter, said sealing diameter being greater than said second end diameter, and a sealing ring, said sealing portion being sized and shaped to be received in said upper well of said female coupling component such that said sealing ring engages said upper well, such that said sealing ring is in a substantially airtight engagement with said upper well interior sidewall surface, and thereby sealing said one or more channels from ambient air.

2. A male coupling component for use in connecting a breast shield with tubing to a vacuum source comprising:
   a first end, wherein said first end is sized and shaped to be attachable to said tubing;
   a second end, wherein said second end has an end diameter and is sized and shaped to be received in a female coupling component, wherein said female coupling component is defined by an interior sidewall surface that is in communication with the vacuum source, wherein said interior sidewall surface has an upper well with a first sidewall diameter, and a lower well and a rim portion between said upper well and said lower well connecting said upper well and said lower well, said lower well including one or more ports formed therein allowing communication of said lower well with the vacuum source, and one or more channels formed therein communicating between said one or more ports and an opening in said rim portion;
   a passageway extending between said first end and said second end; and
   a sealing portion, said sealing portion having a sealing surface formed about a periphery thereof, said sealing portion having a sealing diameter and a sealing ring, said sealing portion being sized and shaped to be received in said upper well of said female coupling component such that said sealing ring engages said upper well, such that said sealing ring is in a substantially airtight engagement with said upper well interior sidewall surface, and thereby sealing said one or more channels from ambient air.

* * * * *